United States Patent
Steffen

(10) Patent No.: US 8,303,483 B2
(45) Date of Patent: Nov. 6, 2012

(54) ADAPTIVE DEVICE AND ADAPTIVE METHOD FOR AUTOMATICALLY ADAPTING THE STOMACH OPENING OF A PATIENT

(76) Inventor: Rudolf Steffen, Bern (CH)

(*) Notice: Subject to any disclaimer, the term of this patent is extended or adjusted under 35 U.S.C. 154(b) by 944 days.

(21) Appl. No.: 12/282,520

(22) PCT Filed: Mar. 12, 2007

(86) PCT No.: PCT/EP2007/052308
§ 371 (c)(1),
(2), (4) Date: Sep. 11, 2008

(87) PCT Pub. No.: WO2007/104745
PCT Pub. Date: Sep. 20, 2007

(65) Prior Publication Data
US 2009/0062826 A1 Mar. 5, 2009

(30) Foreign Application Priority Data
Mar. 13, 2006 (WO) ............... PCT/EP2006/060667

(51) Int. Cl.
*A61F 2/00* (2006.01)
(52) U.S. Cl. ............... 600/37; 604/909; 623/23.65
(58) Field of Classification Search ............ 600/28–32, 600/37; 128/897–899; 623/23.65; 604/909
See application file for complete search history.

(56) References Cited

U.S. PATENT DOCUMENTS

| | | | |
|---|---|---|---|
| 5,938,669 A | 8/1999 | Kkaiber et al. | |
| 6,432,040 B1* | 8/2002 | Meah | 600/37 |
| 6,454,699 B1* | 9/2002 | Forsell | 600/30 |
| 2001/0011543 A1* | 8/2001 | Forsell | 128/899 |
| 2005/0143765 A1* | 6/2005 | Bachmann et al. | 606/157 |

FOREIGN PATENT DOCUMENTS

| | | |
|---|---|---|
| EP | 1600128 A | 11/2005 |
| WO | 0009049 A | 2/2000 |
| WO | 2004012806 A | 2/2004 |

OTHER PUBLICATIONS

International Search Report from corresponding International Application PCT/EP2007/052308.
German Language International Preliminary Report on Patentability (Internationer Vorlaufiger bericht uber die Patentierbarkeit).

* cited by examiner

*Primary Examiner* — Samuel Gilbert
*Assistant Examiner* — Carrie R Dorna
(74) *Attorney, Agent, or Firm* — WRB-IP LLP

(57) ABSTRACT

In an adaptive device and an adaptive method for adapting the stomach opening of a patient, a gastric band having a non-elastic back part on the exterior and a first expandable chamber on the interior are placed around the stomach of the patient for adapting the stomach opening, and the stomach opening of the patient is adapted by modifying the amount of fluid in the first expandable chamber. For this purpose, the adaptive device includes a second expandable chamber, so that the second expandable chamber is connected to the first expandable chamber, and whereby the fluid is displaced from the one expandable chamber to the other expandable chamber in order to modify the stomach opening of the patient. The adaptive device can in particular be controlled by changing the position of the body of the patient.

16 Claims, 5 Drawing Sheets

State of the Art

State of the Art

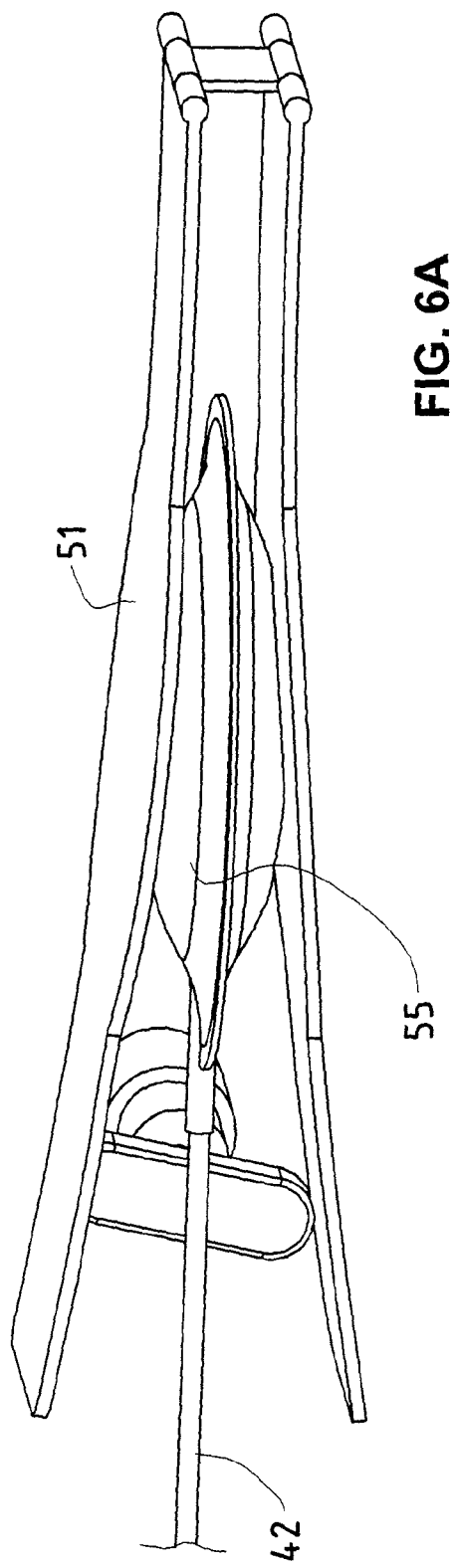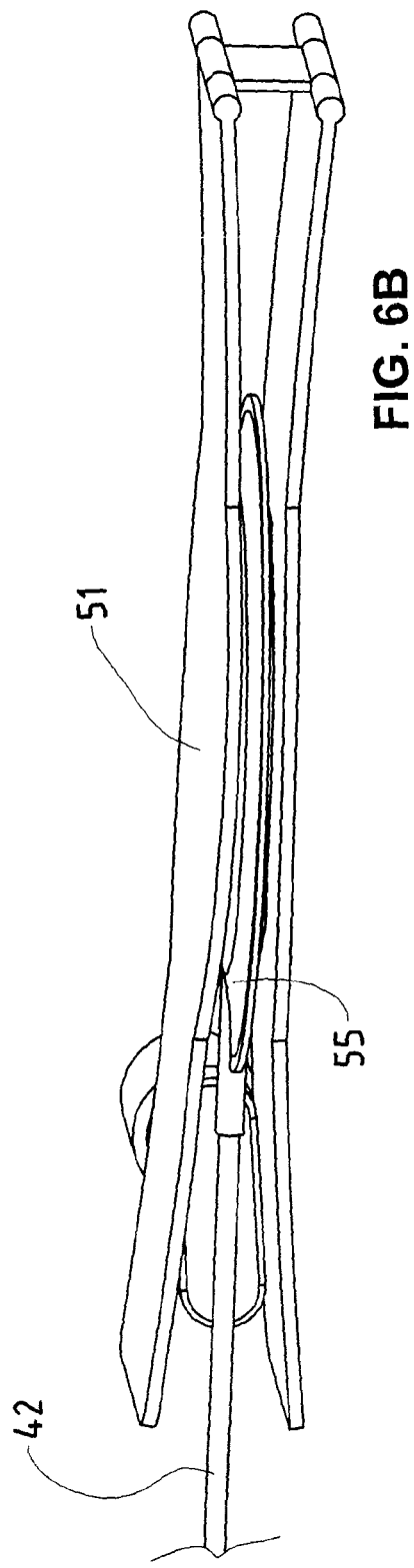

ADAPTIVE DEVICE AND ADAPTIVE METHOD FOR AUTOMATICALLY ADAPTING THE STOMACH OPENING OF A PATIENT

BACKGROUND AND SUMMARY

The invention relates to an adaptive device for automated adaptation of the stomach opening of a patient, comprising a gastric band having a non-elastic back part and a first expandable chamber, and a second expandable chamber connected to the first expandable chamber. The invention relates in particular to an adaptive device for automated adaptation of the stomach opening of a patient in which the gastric band is placeable around the stomach of the patient for adaptation of the stomach opening of the patient, and the fluid is displaceable from the one expandable chamber into the other expandable chamber by means of a conveyance device.

Pathological obesity or adiposity is a bigger and bigger problem in today's modern society. Pathologically obese patients tend toward various so-called sequelae, of which in particular cardiovascular diseases such as high blood pressure, metabolic disturbances such as diabetes or gout, and psychic disorders such as depressions, but also excessive wear and tear of the joint cartilage or elevated cerebral stroke risk play an important role. In this connection, pathological obesity also has an extremely negative effect on the national economy of countries since the expenditures relating both to the direct costs (for doctors' treatment and stationary treatment as well as for the corresponding drugs) as well as to the indirect costs (costs for treatment of the secondary diseases) of the obesity amount in certain countries to almost 10% of the overall costs of the health care system.

Various surgical procedures are known which are used for treatment of pathological obesity. Thus, for example, during a so-called operative bypass, a direct connection is made between the stomach and the small intestine. In this case, a portion of the ingested food does not pass through the whole digestive tract, so that its processing in the body is also to a much lower degree. In another surgical procedure, vertical or horizontal sutures or clamps are put in the stomach wall so that the volume of the stomach is reduced, whereby the quantity or respectively the speed of passage of the ingested food is decreased. The drawbacks of these surgical procedures are that they involve complete operative interventions in the tissue of the patient, which can be very traumatizing for the patient. Moreover it is not rare for complications to arise during such surgical interventions, both before as well as during and after the operation, so that the health of the patient can deteriorate even further.

In another procedure, an inflatable balloon (as a rule made of soft synthetic material) is introduced inside the stomach of the patient. The balloon can thereby be introduced into the stomach of the patient either operatively or without surgical intervention in the compact, unfilled state through the mouth. After the balloon has been inserted in the stomach of the patient, it can be filled with a sterile saline solution through a small inflating hose attached to the balloon. This hose is removed after the filling. The presence of an inflated balloon in the stomach gives the patient a constant feeling of being full, so that ingestion of food takes place less frequently. However, this procedure also has significant drawbacks because the constant contact of the balloon of synthetic material with the inner walls of the stomach can lead to gastric ulcers, intestinal occlusions, or inflammations of the gastric mucous membrane. The balloon can also burst in the stomach of the patient, which is connected with at least considerable discomfort for the patient.

Laparoscopic gastric banding is a further method to combat obesity, in which a flexible band of soft synthetic material (usually silicon) is installed in the upper part of the stomach around the stomach of the patient, so that the stomach is completely wrapped around by the band. The gastric band contains a chamber, which can expand through the addition of fluid, whereby the inner diameter of the gastric band is constricted. On the other hand, the inner diameter of the gastric band can also be enlarged through removal of the fluid from the expandable chamber. To this end, a hose connects the flexible gastric band to a fluid container (also called port chamber or port reservoir), which is installed beneath the skin at an easily accessible place. The advantage of laparoscopic gastric banding is that the patient feels full already after a minimal quantity of food, and is not able to eat further. Moreover the prevalent laparoscopic implantation of the gastric band causes significantly less traumatization of the patient compared with conventional surgical procedures. However, this method also has one significant drawback, namely that the stomach opening of the patient cannot be precisely controlled. Above and beyond this, for adaptation of the stomach opening of the patient, an external intervention must be carried out for addition or removal of fluid (usually through a needle). For this reason, the adaptation of the stomach opening of the patient must performed in each case exclusively by specialized personnel (physicians). It is thus clear that the adaptation of the stomach opening cannot be carried out at any desired time, on the one hand, and, on the other hand, at any desired place. Also the gastric band cannot be adapted to the momentary needs of the patient.

Therefore devices have already been put forward that enable a regulation of the quantity of fluid in a gastric band without external intervention. Such a device is described in the document WO 00/09049, for example. Besides the gastric band with an expandable chamber, this device also comprises a container and a hydraulic means, by means of which the fluid can be shifted out of the container into the gastric band and vice versa. In particular the hydraulic means are designed in such a way that the walls of the container can be shifted to change the volume. However, the hydraulic means in this device must be controlled manually or via a remote control. A registration of the position of the body of the patient or of the pressure on the inner wall of the esophagus of the patient and the dynamic adaptation of the stomach opening based on these variables is therefore not possible.

It is desirable to propose a new device and a new method for automated adaptation of the stomach opening of a patient, which does not have the drawbacks of the state of the art. It is in particular desirable to provide an adaptive device and an adaptive method which make possible a precise, flexible, and simple, completely automated change in the stomach opening of the patient without requiring external intervention, the patient not being able to deliberately influence this change.

In accordance with an aspect of the invention an adaptive device for automated adaptation of the stomach opening of a patient is provided, comprising a gastric band with a non-elastic back part and a first expandable chamber, and a second expandable chamber connected to the first expandable chamber, the gastric band being placeable around the stomach of the patient for adaptation of the stomach opening of the patient, and the fluid being displaceable from the one expandable chamber into the other expandable chamber by means of a conveyance device, a switching device with a sensor module is provided for activation of the conveyance device, a measurement value being able to be registered by means of the sensor module, and the switching device being controllable in an automated way based on the change in the measurement value, a switching device with a sensor module being provided for activation of the conveyance device, a measurement value being able to be registered by means of the sensor module, and the switching device being controllable in an automated way based on the change in the measurement value, the change in the position of the body of the patient or the change in the pressure on the inner wall of the esophagus of the patient being able to be registered by means of the sensor module.

The advantage of such an adaptive device is in particular that the adaptation of the stomach opening of a patient may be carried out in a fully automated way. This adaptation can thereby also take place without outside intervention of any kind. On the one hand, in such an adaptive device, the overall quantity of fluid in the closed system is not changed, which is not the case with the conventional devices. On the other hand, any desired type of control can be built in, so that the quality of life of the patient can be significantly improved without the desired effects in relation to an efficient combating of the morbid obesity being reduced <or> eliminated. Furthermore the automated adaptation of the stomach opening of the patient in such an adaptive device can be controlled merely through the change in the body position of the patient and/or the change in the pressure on the inner wall of the esophagus of the patient (owing to the food located therein). In particular this embodiment variant allows an adaptation of the stomach opening of the patient based on whether the patient is standing up or sitting or lying. Thus the stomach opening of the patient can be somewhat enlarged, for example, during a change from sitting position to lying position. The remains of food still located in the esophagus can thereby be conveyed somewhat more easily into the stomach. This is especially advantageous in the evening and during the night since the patient is thereby able to get much better sleep. Differently, the stomach opening of the patient can be decreased again with change from lying position to sitting or standing position (e.g. in the morning when getting up out of bed), whereby food intake again becomes somewhat more difficult. On the other hand, with excessive pressure on the inner wall of the esophagus of the patient, the patient's stomach opening can be quickly opened a little, whereby the food congestion can be relieved more quickly. The stomach opening can then be likewise narrowed again just as quickly and in just as uncomplicated a manner as soon as the pressure on the inner wall of the esophagus of the patient sinks below a predetermined value. Many known difficulties and problems with food congestion in the esophagus and the upper stomach section with conventional devices can be overcome in an especially advantageous way with this embodiment variant.

In a further embodiment variant, the conveyance device is driven mechanically and/or electrically. This embodiment variant has the advantage, among others, that, with different types of drives, an optimal solution and one adapted to the individual needs of each patient can be sought. The mechanical drive has in particular the advantage that dependence on the power supply can be avoided. By means of a combined mechanical-electrical drive, the adaptive device can moreover be operated in an especially simple way. A purely electrical drive is basically less susceptible to possible malfunctions or failures, whereby a higher degree of reliability of the adaptive for adaptation of the stomach opening of the patient may be achieved.

In another embodiment variant, the conveyance device is designed as a hydraulic pump. This embodiment variant has the advantage, among others, that the fluid between the one expandable chamber and the other expandable chamber can be shifted in an especially advantageous and secure way. Miniaturized hydraulic pumps also exist today, so that the overall size or respectively the overall weight of the adaptive device is not enlarged excessively compared with the conventional devices.

In another embodiment variant, the adaptive device comprises a power storage device for drive of the conveyance device, the conveyance device being electrically connected to the power storage device. This embodiment variant has in particular the advantage that power supply of the conveyance device can take place locally. Thus no external power sources are needed that would make the entire device unusable in the event of a blackout. This embodiment variant can therefore be implemented in an especially advantageous way for adaptation of the stomach opening of the patient.

In still another embodiment variant, the power storage device is rechargeable. This embodiment variant has the advantage, among others, that the power storage device does not need to be replaced after each complete emptying. Depending upon the circumstances, the recharging of the power storage device can also be achieved in contactless ways. Thus through this embodiment variant, not only is the handling of the adaptive device for adaptation of the stomach opening of the patient considerably simplified, but its operational costs are also reduced many times over.

In still another embodiment variant, the adaptive device comprises a line for connection of the first expandable chamber to the second expandable chamber. This embodiment variant has in particular the advantage that the two expandable chambers do not necessarily have to be installed close to each other. In particular it is possible for one of the two expandable chambers not to be a component of the gastric band, but instead to be designed as a discrete unit. By means of a line, the two chambers can then be connected to each other, whereby the necessary communication may be established. Through this embodiment variant, conventional devices for adaptation of the stomach opening of the patient can be converted with relatively minimal changes into adaptive devices according to the invention for adaptation of the stomach opening of the patient, further cost savings being thereby achievable.

In another embodiment variant, the line comprises a valve, the valve being controllable by the switching device. This embodiment variant has in particular the advantage that the shift of the fluid out of the one expandable chamber into the other expandable chamber cannot take place without explicit supervision. Thereby achieved is that the stomach opening is not adapted accidentally, which would cause complications for the patient. The valve can also be designed in particular as a fine adjustment valve, whereby the quantity of fluid that is shifted between the two expandable chambers can be especially precisely controlled. Through a lasting deactivation of the valve, a shift of the fluid between the two expandable chambers can also be made completely impossible, whereby the adaptive device according to this embodiment variant can also be used as a conventional device.

In an again different embodiment variant, a delay module is provided by means of which the activation of the switching device is controllable. The advantage of this embodiment variant lies in particular in that the automated adaptation of the stomach opening of the patient cannot be simply triggered by the patient in that this patient deliberately assumes a lying position for a short time. The delay module according to the invention ensures that the automated change of the stomach opening of the patient does not begin until after a certain time, so that the therapeutic advantages of the adaptive device are in no way affected. Suitable as delay modules are all devices or apparatus that can be implanted in the body of the patient.

In a further embodiment variant, the delay module is programmable. The advantage of this embodiment variant is, among others, that the delay can be set differently for each patient, according to need. Of course, for certain patients, it is necessary to select the delay to be relatively long because they have sleeping problems, thus a premature opening would not be in the interest of the treatment. On the other hand, with certain patients, it is necessary to make the delay as short as possible since they rely on a quick opening, or respectively closing, of the stomach opening. Such a programmable delay module thus makes possible a very simple and reliable individualization and personalization of the adaptive device for automatic adaptation of the stomach opening of the patient.

In a still further embodiment variant, the delay module is programmable and/or controllable by means of a remote control. This embodiment variant has the advantage, among others, that the programming of the delay module (and with it also the length of the delay in the automated adaptation of the stomach opening of the patient) can also be carried out externally without intervention in the body of the patient being necessary therefor. In particular, a continuous improvement of the patient can thereby be accommodated.

In still another embodiment variant, the adaptive device is made substantially of synthetic material. This embodiment variant has the advantage, among others, that the synthetic material has especially advantageous characteristics apparent in particular during the implantation and subsequent functioning of the adaptive device for adaptation of the stomach opening of the patient. Particularly suitable synthetic materials are silicon and silicon elastomers, which have already been successfully used for many other implantable devices.

It should be stated here that, besides the adaptive device according to the invention, the present invention also relates to a corresponding adaptive method for automated adaptation of the stomach opening of the patient.

BRIEF DESCRIPTION OF THE DRAWINGS

Embodiment variants of the present invention will be described in the following with reference to examples. The examples of the embodiments are illustrated by the following attached figures:

FIG. 6 shows the side view of a portion of the device from FIG. 5 for automated adaptation of the stomach opening of a patient.

FIG. 6A shows a portion of the device for automated adaptation of the stomach opening of the patient during enlargement of the stomach opening.

FIG. 6B shows a portion of the device for automated adaptation of the stomach opening of the patient during reduction of the stomach opening.

DETAILED DESCRIPTION

Figure 1:
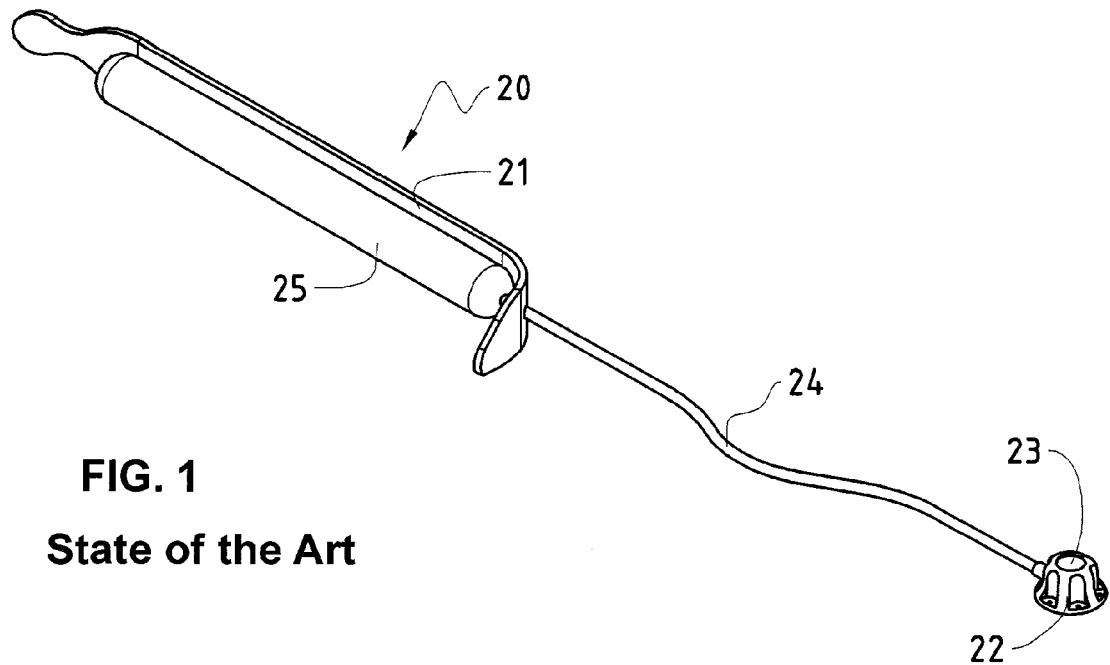
FIG. 1 is a schematic representation in perspective of a device from the state of the art for adaptation of the stomach opening of a patient.

Shown in FIG. 1 is a device from the state of the art for adaptation of the stomach opening of a patient. In FIG. 1, the reference numeral 20 refers to the gastric band, the reference numeral 21 to a non-elastic back part on the outer side of the gastric band 20, and the reference numeral 25 to a first expandable chamber on the inside of the gastric band 20. Moreover the reference numeral 22 refers to the so-called port chamber or port reservoir for receiving fluid, and the reference numeral 23 to the corresponding membrane, which can be pierced percutaneously by means of a needle for supply or removal of fluid. Furthermore, the reference numeral 24 refers to a line, for example a thin tube, which connects the port chamber 22 to the gastric band 20 or respectively to the first expandable chamber 25.

Figure 2:
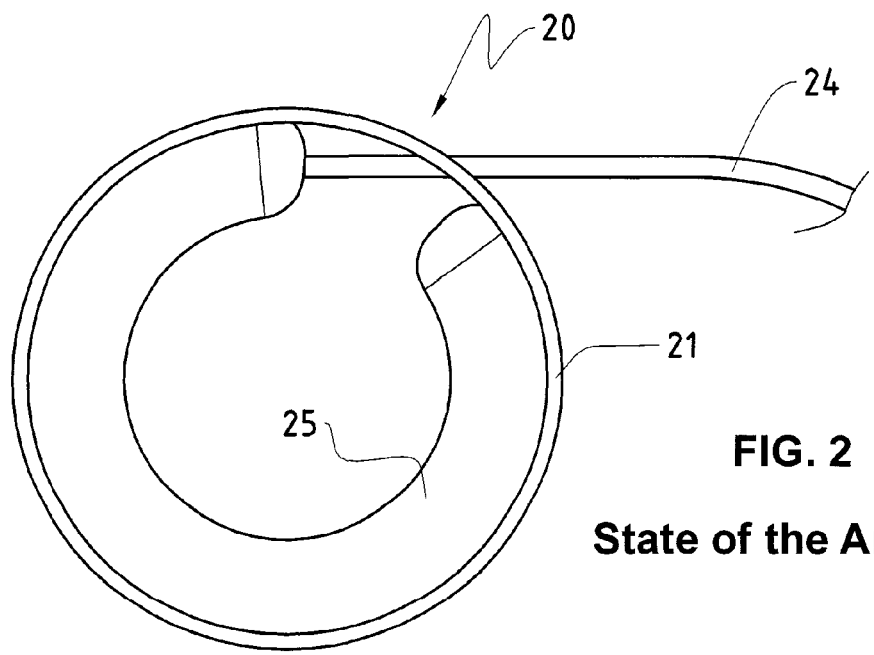
FIG. 2 shows a view from above of a gastric band of a device from the state of the art, in closed state, for adaptation of the stomach opening of a patient.

FIG. 2 illustrates an enlarged cutout of the device for adaptation of the stomach opening of a patient, the gastric band 20 in FIG. 2 being shown in closed state. In closed state, the gastric band 20 forms a loop, the non-elastic back part 21 of the gastric band 20 coming to lie on the outside of the loop, and the first expandable chamber 25 coming to lie on the inside of the loop. The first expandable chamber 25 is connected to the port chamber 22 through the thin tube 24.

Figure 3:
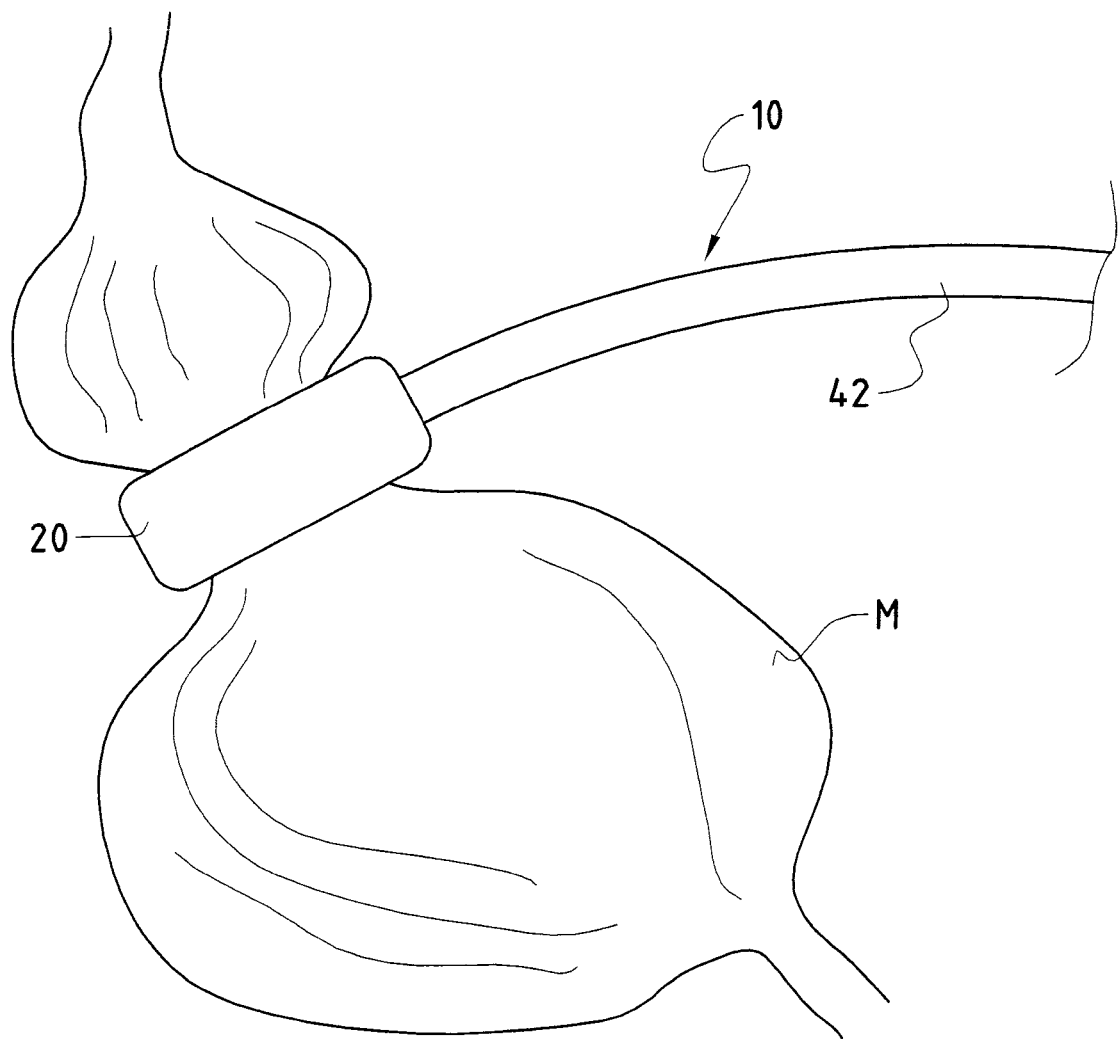
FIG. 3 is a schematic representation in perspective of the stomach of a human body with the implanted device according to the invention for adaptation of the stomach opening of a patient.

In a laparoscopic operation, the gastric band 20 is placed around the upper part of the stomach (M) of the patient, whereby the stomach (M) is divided into two halves, as is shown in a simplified way in FIG. 3. The considerably smaller upper portion (forestomach) is thereby separated from the lower portion (remainder of the stomach) by the artificially created constriction of the gastric band 20. Via the tube 24, the gastric band 20, or respectively the first expandable chamber 25, is connected to the port chamber 22, the port chamber 22 being implanted under the skin. In particular, the abdominal region of the patient is particularly suited for the implantation of the port chamber 22, since obese patients usually have a thick layer of fat below the skin. The filling of the gastric band 20 (or respectively of the first expandable chamber 25) can be controlled, i.e. adapted to the individual needs of each patient, via the connection between the port chamber 22 and the first expandable chamber 25 of the gastric band 20. To fill the gastric band 20, the port chamber 22 or respectively the membrane 23 is punctured through the skin using a fine needle (partially under X-ray control), and fluid is added or removed, whereby the first expandable chamber 25 is either filled or emptied. In this way, the size of the opening of the gastric band 20, i.e. its inner diameter, can be changed, whereby the stomach opening (also called stoma) can be adapted. The gastric band 20 normally consists of or comprises a synthetic material, usually of silicon, whereby other materials would also be conceivable.

Figure 4:
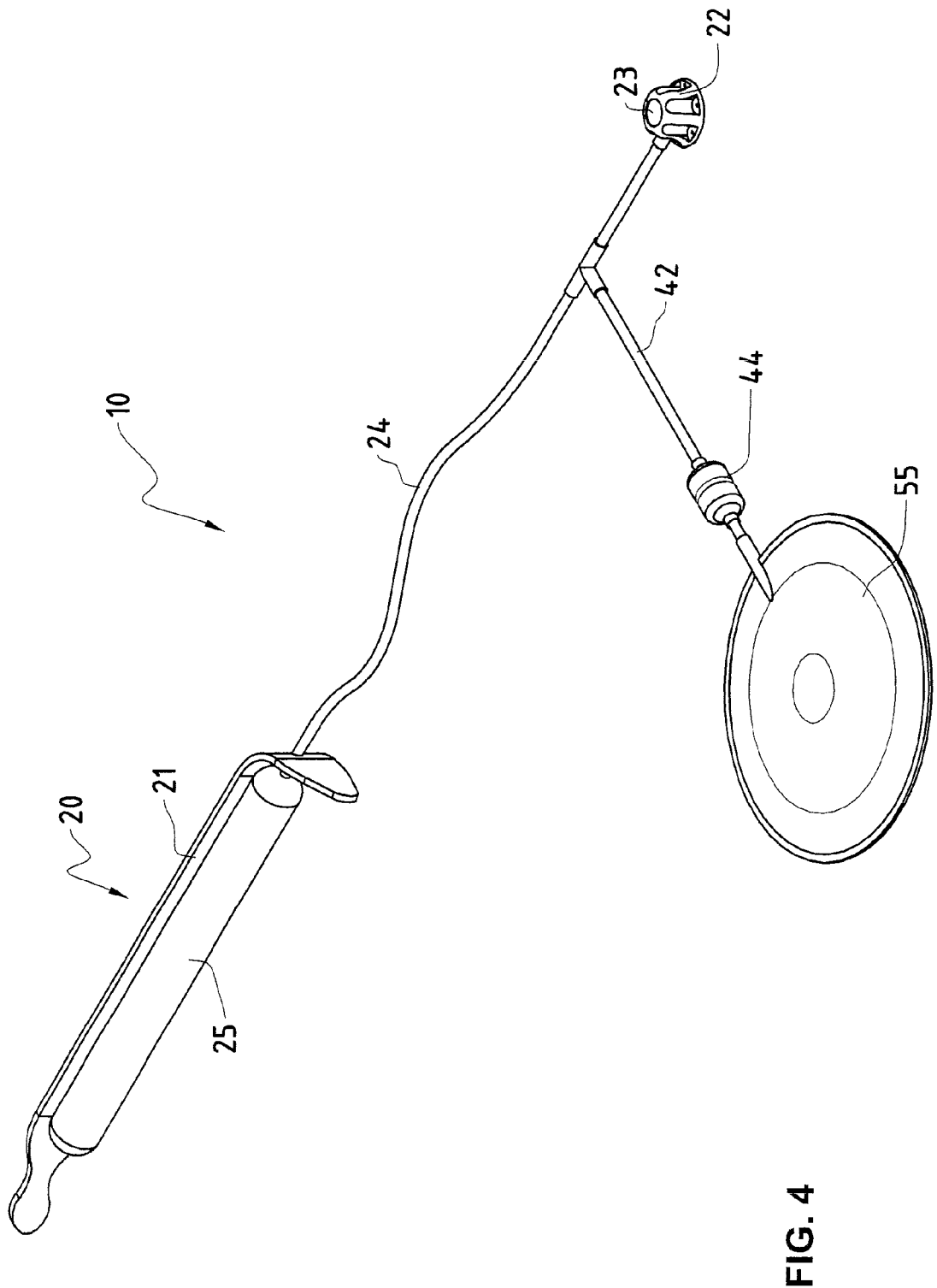
FIG. 4 is a schematic representation in perspective of a device for automated adaptation of the stomach opening of a patient according to one embodiment variant of the present invention.

FIG. 4 illustrates a device for automated adaptation of the stomach opening of a patient according to an embodiment variant of the present invention. In FIG. 4 the reference numeral 20 refers to the gastric band, the reference numeral 21 to a non-elastic back part on the outside of the gastric band 20, and the reference numeral 25 to a first expandable chamber on the inside of the gastric band 20. Furthermore the reference numeral 22 refers to the so-called port chamber or port reservoir for receiving fluid, and the reference numeral 23 to the corresponding membrane, which can be percutaneously pierced by means of a needle for supply or removal of fluid. In addition, the reference numeral 24 refers to a line, for example a thin tube, which connects the port chamber 22 to the gastric band 20 or respectively to the first expandable chamber 25. Moreover in FIG. 4 the reference numeral 55 refers to a second expandable chamber, the reference numeral 42 to a line, for example a thin tube, via which a connection can be established between the second expandable chamber 55 and the first expandable chamber 25, and the reference numeral 44 refers to a valve.

For adaptation of the stomach opening of the patient, the fluid can be shifted out of the first expandable chamber 25 into the second expandable chamber 55, and vice versa, via the lines 24, respectively 42. When, for example, the fluid is shifted out of the first expandable chamber 25 into the second expandable chamber 55, the quantity of fluid in the first expandable chamber 25 is therefore reduced, which, in turn, has the effect of an enlargement of the inner diameter of the gastric band 20. Through this enlargement of the inner diameter of the gastric band 20, the pressure on the stomach (M) of the patient is somewhat reduced, whereby the stomach opening of the patient becomes somewhat enlarged. The ingestion of food in the stomach (M) of the patient can also be thereby eased and accelerated somewhat. On the other hand, when the fluid is shifted in reverse direction out of the second expandable chamber 55 into the first expandable chamber 25, the quantity of fluid in the first expandable chamber 25 thus increases, which, in turn, has the consequence of a reduction of the inner diameter of the gastric band 20. Through this reduction of the inner diameter of the gastric band 20, the pressure on the stomach (M) of the patient also increases somewhat, whereby the stomach opening of the patient becomes somewhat smaller. The ingestion of food in the stomach (M) of the patient thereby turns out to be somewhat more difficult and slower again.

The valve 44 is located on the line 42, for example, by means of which the second expandable chamber 55 is connected to the first expandable chamber 25. Of course the valve 44 can also be located at a different place, as long as its functionality is not thereby limited. The valve 44 can be opened or closed, according to need. A shift of the fluid out of the first expandable chamber 25 into the second expandable chamber can only be made possible at all through an opening of the valve 44. On the other hand, through a lasting closing of the valve 44, a shift of the fluid between the two expandable chambers 25, 55 can be blocked, whereby a device 10 according to the invention for adaptation of the stomach opening of the patient can be used as a conventional device.

The second expandable chamber 55, as certainly also the first expandable chamber 25, can be made of a highly elastic material, so that it has an intrinsic tension. This intrinsic tension of the two expandable chambers 25, 55 can be used for shift of the fluid out of the one expandable chamber 25, 55 into the second expandable chamber 55, 25. Of course the two expandable chambers 25, 55 should have in this case an opposing tension (the first chamber 25 is taut when the second expandable chamber 55 is slack and vice versa).

Figure 5:
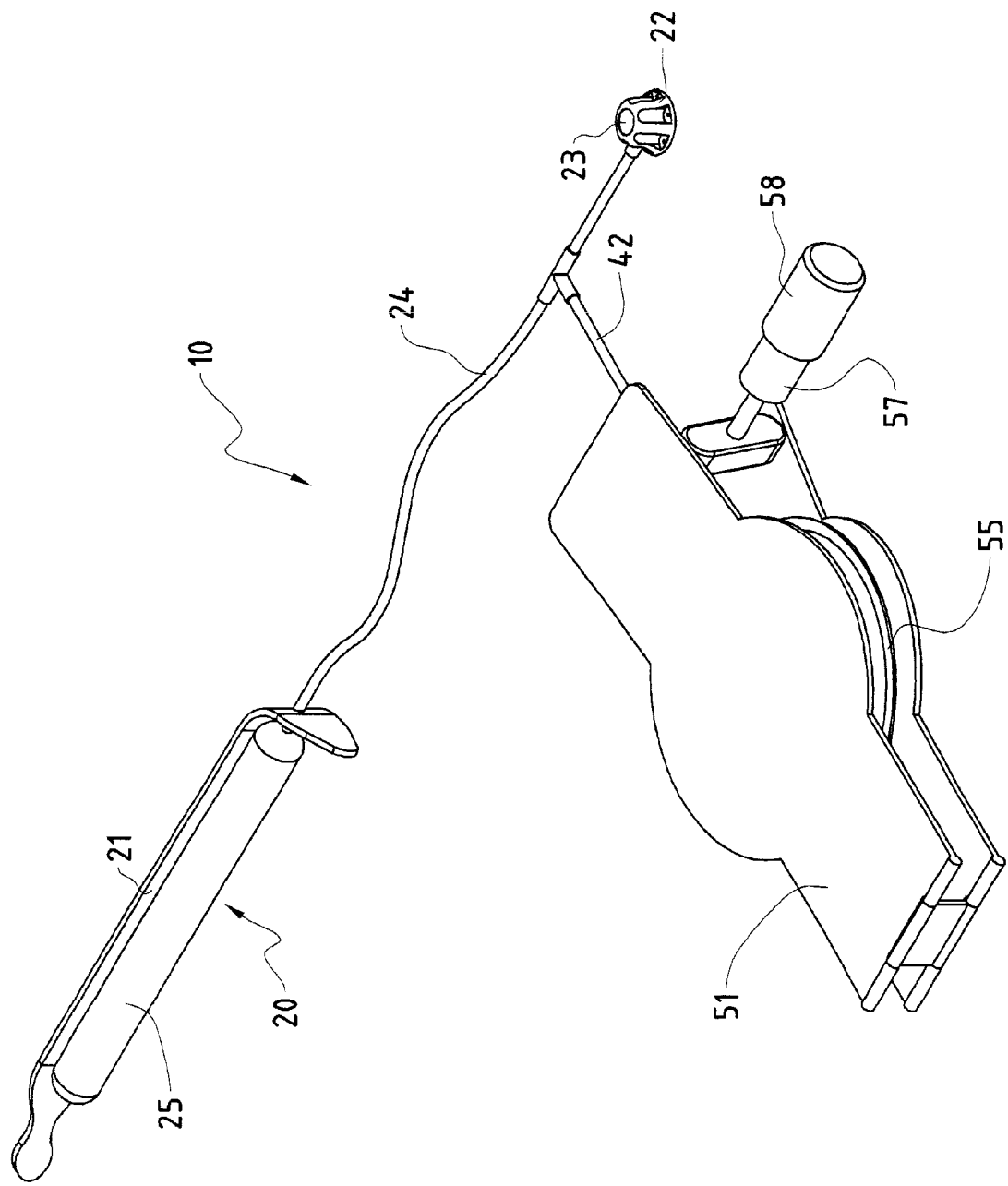
FIG. 5 is a schematic representation in perspective of a device for automated adaptation of the stomach opening of a patient according to a further embodiment variant of the present invention.

FIG. 5 illustrates a device for automated adaptation of the stomach opening of a patient according to another embodiment variant of the present invention. In FIG. 5, the reference numeral 20 refers again to the gastric band, the reference numeral 21 to a non-elastic back part on the outside of the gastric band 20, and the reference numeral 25 refers to a first expandable chamber on the inside of the gastric band 20. Moreover the reference numeral 22 refers again to the so-called port chamber or port reservoir for receiving fluid, and the reference numeral 23 to the corresponding membrane, which can be pierced percutaneously by means of a needle in each case for supply or removal of fluid. Furthermore, the reference numeral 24 refers again to a line, for example a thin tube, which connects the port chamber 22 to the gastric band 20 or respectively to the first expandable chamber 25. The reference numeral 55 refers again to a second expandable chamber, and the reference numeral 42 to a line, for example a thin tube, via which a connection can be established between the second expandable chamber 55 and the first expandable chamber 25. In FIG. 5, the reference numeral 51 refers to a conveyance device which can be used for active shift of the fluid out of the one expandable chamber 25, 55 in the other expandable chamber 55, 25, the reference numeral 57 to a switching device for activation of the conveyance device 51, and the reference numeral 58 to a power storage device, which can be used, for example, for drive of the conveyance device 51.

As already in the embodiment variant from FIG. 4, the fluid can be shifted out of the first expandable chamber 25 into the second expandable chamber 55 and vice versa via the lines 24, respectively 42, for adaptation of the stomach opening of the patient. By means of the conveyance device 51, this shift of the fluid between the two expandable chambers 25, 55 can also be driven actively. In the example shown, the conveyance device 51 conveys the fluid out of the second expandable chamber 55 to the first expandable chamber 55 mechanically. The conveyance device 51 consists of or comprises two plates of made of a hard material (for example steel), which are tensioned in such a way that they are pressed against each other in normal state (i.e. without impact from outer influences). The second expandable chamber 55 is located between the two plates of the conveyance device 51, and is under pressure in the normal state of the conveyance device 51. In the normal state of the conveyance device 51, the fluid is thus shifted out of the second expandable chamber 55 into the first expandable chamber 25. If need be, this displacement can be blocked by the valve 44, which is located on the line 42 between the second expandable chamber 55 and the first expandable chamber 55 <sic. 25>, according to need.

In FIG. 5 the reference numeral 58 refers to a power storage device. The power storage device 58 can store the electrical energy that is needed for operation of the conveyance device 51. For this purpose, the power storage device 58 is electrically connected to the conveyance device 51 and/or to the switching device 57. This power storage device 58 can be rechargeable, or can be replaced after each emptying. In particular the power storage device 58 can be a lithium-ion battery.

In FIG. 5, the reference numeral 57 refers to a switching device by means of which the conveyance device 51 can be activated or respectively controlled. The switching device 57 in FIG. 5 is connected to a cam disk which is also situated between the two plates of the conveyance device 51. The cam disk is set in motion by means of the switching device 57, whereby a pressure is exerted on the plates of the conveyance device 51, and the plates are pushed apart. The pressure on the second expandable chamber 55, likewise situated between the two plates of the conveyance device 51, is thereby also reduced, so that the fluid can flow back out of the first expandable chamber 25 into the second expandable chamber 55. FIG. 6A shows the conveyance device 51 in a side view, when the plates of the conveyance device 51 are pushed apart by means of the cam disk, so that the second expandable chamber 55 can expand, by virtue of the intrinsic tension. On the other hand, FIG. 6B shows the opposite situation in which the second expandable chamber 55 is pressed together by the two plates of the conveyance device 51. Of course this shift of fluid can also be blocked by means of the valve 44, if need be.

However, we would like to point out here that both the conveyance device 51 and the switching device 57 or any other elements of the adaptive device according to the invention for adaptation of the stomach opening of the patient can of course also have other forms or modes of operation. Thus, for example, in particular the conveyance device 51 can also be a hydraulic or other pump, or another device of another kind, by means of which the fluid can be shifted back and forth between the two expandable chambers 25, 55.

The switching device 57 can be controlled in an automated way, in particular based on the change in a measurement value. For this purpose, the switching device 57 comprises a sensor module for registration of this measurement value. Based on the value of this measurement value, or respectively based on the change in this measurement value, the switching device 57 can be controlled automatically. This sensor module can of course also be placed in a different location, however, and can be connected to the switching device 57 in a wired or wireless way. The measurement value registered by the sensor module can be in particular the position of the body of the patient. In this case, the switching device 57 can be controlled through the position of the body of the patient in such a way that with an upright (standing or sitting) body position, the gastric band 20 has a small inner diameter, whereby the stomach opening of the patient is kept small. This body position corresponds namely to the normal position of the patient during the day, in which the problems relatively rarely arise. With a change of body position from an upright into a horizontal position (lying), the switching device 57 can be set in such a way that the inner diameter of the gastric band 20 becomes somewhat larger, so that the stomach opening of the patient becomes somewhat larger. Ingestion of food can thereby be somewhat eased, so that no food bottlenecks arise in the esophagus of the patient. A similar effect can also be achieved by the switching device 57 being controlled by the change in the pressure on the inner wall of the esophagus of the patient. With a pressure above a predefined level, the stomach opening of the patient can be enlarged through the shift of the fluid out of the first expandable chamber 25 into the second expandable chamber 55, or vice versa. Many problems connected with the use of the gastric bands 20 can thereby be eliminated.

On the other hand, it must be prevented that the patient deliberately triggers the automated adaptation of the stomach opening in order to influence the therapy through trickery, for instance. Thus the patient could place himself briefly in the lying position, for example, and thus bring about the opening of the stomach opening. Of course the automated adaptation of the stomach opening would not fulfill the original goal in this case. Therefore a delay module can be provided in the device according to the invention, by means of which delay module the activation of the switching device can be controlled. Thus the adaptation of the stomach opening of the patient can be initiated only after a start delay of half an hour, for example. During this delay period, activation of the conveyance device 51 would be impeded, even though a corresponding activation should be carried out based on the signals of the sensor module of the switching device 57. Of course this delay can be variably configured, for instance by the delay time being somewhat greater with the enlargement of the stomach opening than the delay time for the closing of the stomach opening of the patient. The delay time can also be set to zero in the one case or the other, whereby there would be no delay. This delay time can be defined and programmed a single time before the implantation; however, delay modules can also be provided that are able to be programmed and unprogrammed as desired. At the same time this programming or respectively control of the delay module can also be carried out by means of a remote control. This remote control can be achieved by means of an external transmitter and an implantable receiver, for example, the implantable receiver being connected to the delay module. Radio waves can be used for signal transmission, for example. By means of a remote control, the delay time can be changed as needed (also only temporarily) without external intervention being necessary.

In conclusion, it is to be pointed out that the embodiment variants described by way of example represent only a selection of possible embodiments of the inventive concept, and should not be viewed in any way as limiting. One skilled in the art will understand that many other ways of implementing the invention are possible without the essential features of the invention being lost sight of.

The invention claimed is:

1. An adaptive device for automated adaptation of a stomach opening of a patient, comprising
a gastric band with a non-elastic back part and a first expandable chamber, and a second expandable chamber connected to the first expandable chamber, the gastric band being placeable around the stomach of the patient for adaptation of a stomach opening of the patient, and fluid being displaceable from the first expandable chamber into the second expandable chamber by a conveyance device, and
a switching device with a sensor module for activation of the conveyance device, a measurement value being able to be registered by the sensor module, and the switching device being arranged to be automatically controlled without external intervention based on a change in the measurement value, wherein the measurement value corresponds to a change in a position of a body of the patient, the switching device comprising a delay module for delaying activation of the conveyance device for a predetermined length of time after the change in measurement value.

2. The adaptive device according to claim 1, wherein the conveyance device is driven mechanically and/or electrically.

3. The adaptive device according to claim 1, wherein the conveyance device is a hydraulic pump.

4. The adaptive device according to claim 1, wherein the adaptive device comprises a power storage device for driving the conveyance device, the conveyance device being electrically connected to the power storage device.

5. The adaptive device according to claim 4, wherein the power storage device is rechargeable.

6. The adaptive device according to claim 1, wherein the adaptive device comprises a line for connection of the first expandable chamber to the second expandable chamber.

7. The adaptive device according to claim 6, wherein the line comprises a valve, the valve being controllable by the switching device.

8. The adaptive device according to claim 1, wherein the adaptive device is made substantially of synthetic material.

9. The adaptive device according to claim 1, wherein the switching device is arranged to be automatically controlled based on a change in pressure on an inner wall of an esophagus of the patient.

10. An adaptive method for automated adaptation of a stomach opening of a patient, comprising placing a gastric band with a non-elastic back part and a first expandable chamber around the stomach of the patient for adaptation of the stomach opening of the patient, displacing fluid from the first expandable chamber into a second expandable chamber by a conveyance device, registering a measurement value by a sensor module, and controlling a switching device automatically and without external intervention based on a change in the measurement value to activate the conveyance device, wherein the change in the measurement value corresponds to a change in a position of a body of the patient, the switching device being automatically controlled to activate the conveyance device only after a delay for a predetermined length of time after the change in measurement value.

11. The adaptive method according to claim 10, comprising driving the conveyance device mechanically and/or electrically.

12. The adaptive method according to claim 10, wherein the conveyance device is a hydraulic pump.

13. The adaptive method according to claim 10, wherein the conveyance device is electrically connected to a power storage device.

14. The adaptive method according to claim 10, wherein the first expandable chamber is connected to the second expandable chamber by a line.

15. The adaptive method according to claim 14, wherein a valve of the line is controlled through the switching device.

16. The adaptive method according to claim 10, comprising controlling the switching device automatically based on a change in pressure on an inner wall of an esophagus of the patient.

\* \* \* \* \*